United States Patent [19]
Thompson

[11] 4,085,047
[45] Apr. 18, 1978

[54] BLOOD LEAK DETECTOR

[76] Inventor: Lester E. Thompson, 10850 Kingsley Rd., Apt. 228, Dallas, Tex. 75238

[21] Appl. No.: 723,924

[22] Filed: Sep. 16, 1976

[51] Int. Cl.² .................. B01D 19/00; G01J 3/50
[52] U.S. Cl. .................................. 210/96 M; 55/185; 210/188; 250/576; 356/181
[58] Field of Search ................. 55/52, 159, 185; 128/214 R; 210/22, 94, 96 M, 321 B, 188; 250/573, 576; 356/39, 181

[56] References Cited

U.S. PATENT DOCUMENTS

| | | | |
|---|---|---|---|
| 3,506,126 | 4/1970 | Serfass et al. | 210/321 B X |
| 3,544,798 | 12/1970 | Topol | 250/573 |
| 3,606,539 | 9/1971 | Polanyi et al. | 356/39 |
| 3,802,562 | 4/1974 | Kozlov et al. | 210/96 M |
| 3,803,810 | 4/1974 | Rosenberg | 55/159 |
| 3,809,243 | 5/1974 | Teders | 210/96 M |
| 3,832,067 | 8/1974 | Kopf et al. | 356/181 |
| 3,861,802 | 1/1975 | Belmear, Jr. | 250/573 X |
| 3,900,396 | 8/1975 | Lamadrid | 210/94 |
| 3,912,468 | 10/1975 | Tsuchiya et al. | 55/159 |

Primary Examiner—Charles N. Hart
Assistant Examiner—Robert H. Spitzer
Attorney, Agent, or Firm—Richards, Harris & Medlock

[57] ABSTRACT

A blood leak detector includes a housing having top and bottom walls and opposed end walls. Dialysate fluid is received in the housing through a port formed in the bottom wall and is directed upwardly through the housing to an outlet port formed in the top wall at a point directly above the inlet port. Axially aligned cylindrical plugs are mounted in the end walls. One of the plugs houses structure for directing a beam of green light through the effluent dialysate and the other cylindrical plug houses structure responsive to green light for generating an ouptput signal indicative of the opacity of the dialysate. A 70 micron stainless steel screen is wrapped around the cylindrical plugs and functions to prevent gas bubbles flowing into the housing with the dialysate from entering the light beam. The cylindrical screen extends to opposed edges positioned in a spaced apart relationship to define a slot which permits gas flow out of the interior of the cylindrical screen configuration.

6 Claims, 4 Drawing Figures

BLOOD LEAK DETECTOR

BACKGROUND AND SUMMARY OF THE INVENTION

This invention relates to blood leak detectors, and more particularly to blood leak detectors that are useful in hemodialysis systems.

During the course of hemodialysis treatment, blood is circulated through an artificial kidney in close proximity to a dialysate comprising a prepared chemical solution designed to cleanse the blood of organic wastes and excess fluids and to equalize the chemical balance of the blood. These results are accomplished utilizing a membrane which separates the blood from the dialysate and acts as a medium of transfer. The membrane is constructed to permit the required fluid flow therethrough while preventing the loss of whole blood into the dialysate. A persistent problem in hemodialysis treatment is the possibility of either blood leaking through or complete rupture of the membrane of the artificial kidney. Any such occurrence results in blood loss from the patient being treated with consequences which range from insignificant to extremely serious. It is therefore critical to monitor the dialysate flowing from an artificial kidney to detect the presence of blood therein and to actuate an alarm if more than a predetermined amount of blood is detected in the effluent dialysate.

Almost all hemodialysis systems heretofore provided have been equipped with blood leak detectors. However, the blood leak detectors heretofore available have exhibited numerous problems. For example, effluent dialysate is characterized by both liquids and gas bubbles flowing with the liquids. In prior blood leak detectors, these gas bubbles have frequently caused false actuations of the alarm system. Another problem that has characterized prior blood leak detectors is the rapid contamination thereof by waste materials. Another disadvantage has been the failure of blood leak detectors to recognize the optical characteristics of blood and to take advantage thereof to provide a system that is highly reliable in operation.

The present invention comprises a blood leak detector which overcomes the foregoing and other disadvantages which have long since characterized the prior art. In accordance with the broader aspects of the invention, a screen is utilized to remove gas bubbles from the flowing liquid of the dialysate. By this means false triggerings of the alarm of the system are completely eliminated. A beam of green light is directed through the liquid of the dialysate, and a photosensitive device responsive to green light is utilized to generate output signals indicative of the opacity of the liquid. Due to the optical characteristics of blood, the use of a beam of green light to test the opacity of the dialysate liquid has been found to substantially increase the reliability of the system. The screen and the light beam generating and detecting systems are mounted in a housing and are positioned substantially above the bottom thereof. Foreign materials may therefore be accumulated in the bottom of the housing without interfering with the operation of the system.

In accordance with more specific aspects of the invention, the green light beam generating system and the light beam detecting system are mounted in cylindrical plugs which extend into the opposite ends of the housing. The screen comprises a 70 micron stainless steel screen which is wrapped around the cylindrical plugs to form a cylindrical configuration. The screen is provided with a slot at the top thereof to permit gases to escape from the interior of the cylindrical configuration of the screen. The screen is positioned directly in the path of dialysate flow through the housing and functions to permit liquid to pass through the green light beam while preventing bubbles from entering the light beam and thereby generating false output signals from the light sensitive device.

The blood leak detector of the present invention is preferably utilized in a blood leak detector system including a reference blood leak detector which receives fresh dialysate flowing to an artificial kidney and a monitor blood leak detector which receives effluent dialysate flowing from the artificial kidney. The outputs from the reference blood leak detector and the monitor blood leak detector are directed to a comparator circuit which functions to compare the two outputs. Whenever the output of the monitor blood leak detector goes off normal as compared with the output of the reference blood leak detector, the comparator circuit actuates an alarm which indicates that blood has been detected in the effluent dialysate flowing from the artificial kidney.

DESCRIPTION OF THE DRAWINGS

A more complete understanding of the invention may be had by reference to the following Detailed Description when taken in conjunction with the accompanying Drawings, wherein.

DETAILED DESCRIPTION

Figure 1:
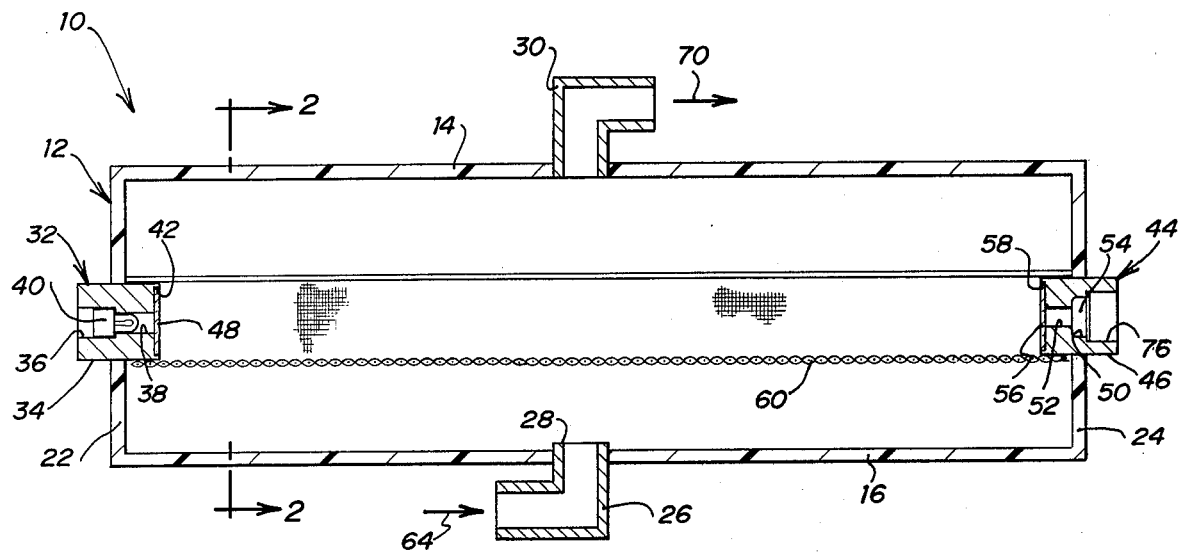
FIG. 1 is a longitudinal sectional view of a blood leak detector incorporating the invention.

Referring now to the Drawings, and particularly to FIG. 1 thereof, there is shown a blood leak detector 10 incorporating the invention. The blood leak detector 10 comprises a housing 12 which may be formed from any of various materials, such as plastic sheet material. For example, the housing 12 may be formed from polypropylene or any other FDA approved type of plastic sheet material. The various sections of plastic sheet material which are utilized to form the housing 12 are preferably adhesively secured together or are otherwise joined so as to form a housing which is entirely liquid and gas tight. Also, all of the sections of plastic material which are utilized to form the housing 12 must be entirely opaque to the transmission of visible light.

The housing 12 comprises a top wall 14, a bottom wall 16, a pair of side walls 18 and 20, and a pair of end walls 22 and 24. Bottom wall 16 has a liquid inlet 26 mounted therein. The inlet 26 preferably projects into the interior of the housing 12 slightly beyond the interior surface of the bottom wall 16 to provide an upstanding lip 28. The top wall 14 has an outlet 30 mounted therein. The inner end of the outlet 30 is preferably at least flush with the interior surface of the top wall 14, and may be recessed into the top wall 14 if desired. This is to prevent any trapping of gases within the housing 12 adjacent the interior surface of the top wall 14.

A light source assembly 32 extends through the end wall 22 and is sealed therein. The light source assembly 32 comprises a plug 34 having a relatively large diameter bore 36 formed therein which extends to a small diameter bore 38. An electric lamp 40 is mounted in the bore 36 and extends into the bore 38. A green filter 48 is mounted in a recessed portion 42 of the plug 34 and is sealed therein.

A detector assembly 44 is mounted in the end wall 24 of the housing 12 and is sealed therein. The detector assembly 44 comprises a plug 46 having a large diameter bore 76 formed therein which extends to an intermediate diameter bore 50 which in turn extends to a small diameter bore 52. A photosensitive device 54 which may comprise a photocell or the like is mounted in the bore 50 in communication with the bore 52. A light transparent filter 56 is mounted in a recess 58 formed in the plug 46 and is sealed therein.

Figure 2:
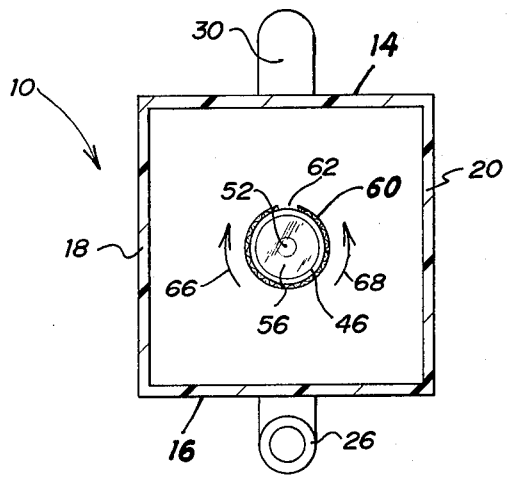
FIG. 2 is a transverse sectional view taken generally along sectional lines 2—2 of FIG. 1 of the blood leak detector shown in FIG. 1.

The plug 34 comprising the light source assembly 32 and the plug 46 comprising the detector assembly 44 are preferably equal in diameter. Referring to FIG. 2, a screen 60 is wrapped tightly around the plugs 34 and 46 so as to assume a cylindrical configuration. An important feature of the present invention comprises a gap 62 which is formed between the opposed edges of the screen 60 when the screen is wrapped around the plugs 34 and 46. By way of example, the screen 60 may comprise a 70 micron screen formed from an FDA approved type of stainless steel. This type of screen may be utilized in the practice of the present invention by forming the plugs 34 and 46 to an outside diameter of 1 inch, and providing a ¼ inch gap 62 between the adjacent edges of the screen 60 after the screen 60 is wrapped around the plugs 34 and 46.

In the utilization of the blood leak detector 10, fluid of the type used in hemodialysis is admitted to the housing 12 through the inlet 26 in the manner indicated by the arrow 64. Such fluid is primarily liquid which passes directly through the screen 60 and into the path of light passing from the light source assembly 32 to the detector assembly 44. Due to the use of the green filter 48 in the light source assembly 32, this light is green in color. The photosensitive device 54 utilized in the detector assembly 44 is sensitive to green light. The use of the green filter 48 and the use of a green light sensitive device 54 is due to the fact that green is within the absorption band of blood.

Assuming first that the fluid flowing into and through the housing 12 is entirely free of blood, the photosensitive device 54 of the detector assembly 44 produces a predetermined output responsive to light transmitted from the light source assembly 32. Assuming now that blood is present in the fluid flowing through the housing 12, the output from the device 54 is changed in a very pronounced manner, whereby the presence of blood in the fluid is rapidly and efficiently detected. Because green is within the absorption band of blood, the use of a green filter in the light source assembly 32 and the use of a green light responsive photosensitive device 54 in the detector assembly 44 markedly increases the reliability of the operation of the blood detector 10 of the present invention.

In the operation of a hemodialysis system, gases in the form of bubbles are frequently introduced into the flowing liquid. Assuming that bubbles of gas enter the housing 12 through the inlet 26, such gas bubbles do not pass through the screen 60, but instead flow around the perimeter of the screen 60 in the manner indicated by the arrows 66 and 68 in FIG. 2. Such gas bubbles then pass out of the housing 12 through the outlet 30 in the direction indicated by the arrow 70 (FIG. 1) with the flowing liquid. Due to the fact that the outlet 30 does not project into the interior of the housing 12, no gases are permitted to be accumulated within the interior of the housing 12.

The removal of gases from the interior of the housing 12 is also promoted by the use of the gap 62 (FIG. 2) between the adjacent edges of the screen 60. Thus, during initiation of the operation of the blood detector 10 it is possible for gases to accumulate within the interior of the screen 60. However, as soon as liquid begins to flow through the interior of the housng 12 and through the screen 60, such gases are immediately removed from the interior of the screen 60 through the gap 62. Thus, it will be understood that the use of the gap 62 and the screen 60 prevents any accumulation whatsoever of gas bubbles within the interior of the screen 60, and thereby completely negates the possibility of gas bubbles blocking the path of light transmission from the light source assembly 32 to the detector assembly 44.

Due to the positioning of the inlet 26 at the bottom of the housing 12, and due to the positioning of the outlet 30 at the top of the housing 12, it will be understood that the general direction of fluid to flow through the housing 12 is upward, and therefore perpendicular to the path of light transmission from the light source assembly 32 to the detector assembly 44. Due to the positioning of the screen 60 in the path of liquid flow through the housing 12, liquid entering the housing 12 through the inlet 26 tends to spread outwardly along the entire length of the housing 12, whereby liquid is caused to flow upwardly across the exterior surfaces of the lens 48 of the light source assembly 32 and the lens 56 of the detector assembly 44. By this means the fluid flow through the housing 12 is advantageously utilized to continuously clean the exterior surfaces of the lenses 48 and 56, thereby further promoting light transmission from the light source assembly 32 to the detector assembly 44. It will be noted in this regard that the positioning of the inner end surfaces of the light source assembly 32 and the light source assembly 44 well into the interior of the housing 12 further promotes the cleaning effect of fluid flow across the end exterior surfaces of the lenses 48 and 56.

Figure 3:
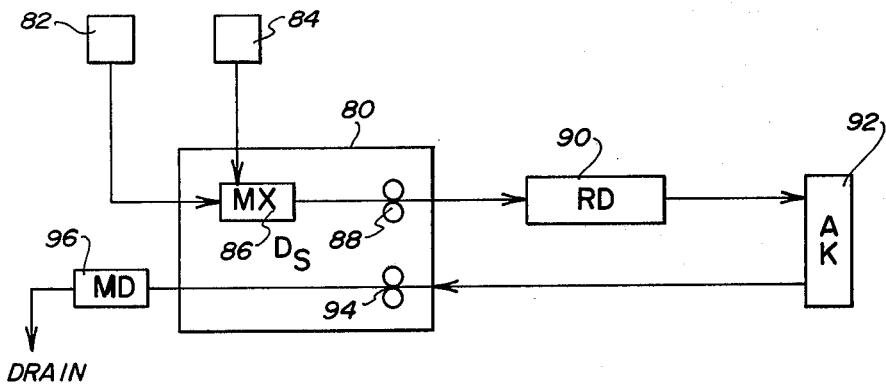
FIG. 3 is a schematic illustration of a hemodialysis system incorporating a blood leak detector system comprising the present invention.
Figure 4:
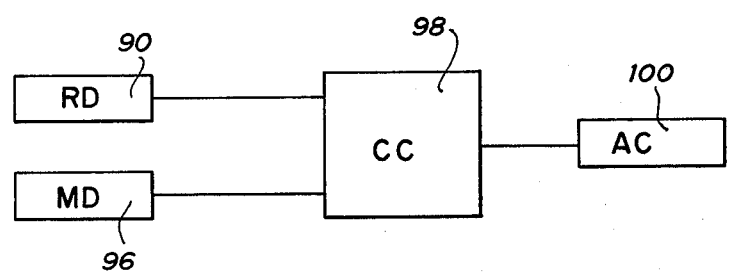
FIG. 4 is a further illustration of the blood leak detector system of FIG. 3.

Referring now to FIGS. 3 and 4, the use of the blood detector 10 of the present invention is further illustrated. A delivery system 80 receives a medically prescribed type of dialysate concentrate from a source 82. The delivery system 80 also receives water from a source 84. It will be understood that in certain systems, the concentrate and the water are premixed prior to entry into the delivery system 80.

Concentrate from the source 82 and water from the source 84 are received in the delivery system 80 in a mixing valve 86. The mixing valve 86 mixes the concentrate into the water in the correct proportions to provide dialysate to be utilized in hemodialysis. The dialysate is directed through a pump 88 to a reference detector 90 which comprises a blood detector of the type described hereinbefore in connection with FIGS. 1 and 2. From the reference detector 90 the dialysate is directed to an artificial kidney 92 wherein it is utilized to effect hemodialysis.

Effluent from the artificial kidney 92 is returned to the delivery system 80 and is received by a pump 94. From the pump 94 the effluent dialysis is directed to a monitor detector 96 which is also identical to the blood detector 10 described hereinbefore in connection with FIGS. 1 and 2. From the monitor detector 96 the effluent dialysis is directed to a drain.

Referring to FIG. 4, the output from the photosensitive device 54 of the detecting circuit 44 (FIG. 1) of the reference detector 90 and the output from the photosensitive device 54 of the detecting circuit 44 of the monitor detector 96 are directed to a comparator circuit 98. In the calibration of the system, the outputs of the photosensitive devices 54 of the reference detector 90 and the monitor detector 96 are adjusted so as to be balanced during normal operation. Assuming now that blood is present in the effluent dialysis flowing through the monitor detector 96, the output from the photosensitive device 54 thereof goes off normal. This causes the comparator circuit to generate an output which actuates an alarm circuit 100. Actuation of the alarm circuit 100 is indicative of the fact that blood has been detected in the effluent dialysate flowing out of the artificial kidney 92.

Responsive to actuation of the alarm circuit 100, various corrective steps are immediately initiated. First, the operation of the delivery system 80 is terminated, thereby preventing further input of dialysate to the artifical kidney 92. Simultaneously the flow of blood into the artificial kidney 92 is terminated. Other results of actuation of the alarm circuit 100 include initiation of the operation of a visual alarm and initiation of the operation of an audible alarm.

From the foregoing, it will be understood that the present invention includes numerous advantages over the prior art. Referring to FIG. 3 of the Drawings, one advantage to the use of the present invention involves the fact that the reference detector 90 may be utilized on the high pressure side of the pump 88, and the fact that the monitor detector 96 may be utilized on the high pressure side of the pump 94. This has been found to be highly advantageous in reducing the presence of gas bubbles in the fluid flowing through the blood detector of the present invention. Another advantage in the use of the invention involves the fact that the use of the screen 60 thereof, and particularly the use of a cylindrical screen configuration functions to allow liquid flow through the light path between the light source assembly 32 and the detector assembly 44 while separating gas bubbles from the flowing liquid and causing the gas bubbles to flow around the light path. By thus preventing gas bubbles from entering the light path between the light source assembly 32 and the detector assembly 44, the use of the present invention eliminates false triggering of the alarm circuit 100 which has frequently characterized prior art devices. Still another advantage deriving from the use of the present invention involves the use of the slot 62 between the adjacent ends of the screen 60, whereby gas which might be present in the system at start-up or otherwise is allowed to escape with the liquid flowing therethrough. The use of the present invention is clearly advantageous in that a green filter 48 is utilized in the light source assembly 32 and a green light responsive photosensitive device 54 is utilized in the detector assembly 44, whereby the reliability of operation of the blood detector 10 is substantially increased. Yet another advantage deriving from the use of the present invention involves the fact that due to the construction of the housing 12, opaque or substantially opaque contaminants may accumulate in the bottom thereof without interfering with the passage of light between the light source assembly 32 and the detector assembly 44. This includes solid particles of blood which may enter the housing 12 at the time of a blood leak, but which are incapable of passing through the screen 60. Other advantages to the use of the invention will readily suggest themselves to those skilled in the art.

Although preferred embodiments of the invention have been illustrated in the accompanying Drawing and described in the foregoing Detailed Description, it will be understood that the invention is not limited to the embodiments disclosed, but is capable of numerous rearrangements, modifications, and substitutions of parts and elements without departing from the spirit of the invention.

What is claimed is:

1. A blood leak detector comprising:
    a housing including a top wall, a bottom wall, opposed side walls and opposed end walls;
    means for preventing ambient visible light from entering the interior of said housing;
    inlet means projecting into the interior of said housing through said bottom wall for directing fluid containing blood and gas bubbles into said housing;
    oulet means contained within said top wall of said housing for directing fluid including blood and gas bubbles contained therein out of said housing through said top wall at a position located directly above the position of entry of said fluid into said housing through said inlet means;
    means for generating a beam of light mounted in one of said end walls of said housing;
    means for detecting said beam of light mounted in the other one of said end walls of said housing;
    said light beam generating means and said light beam detecting means comprising axially aligned cylindrical plugs of substantially equal diameter mounted and contained within said opposed end walls of said housing;
    screen means mounted within said housing extending between said axially aligned cylindrical plugs, dimensioned and oriented for mating with said cylindrical plugs to form a cylindrical configuration;
    said screen means having spaced apart edges defining a slot therebetween mounted at the top of said cylindrical configuration to permit the escape of gas bubbles from the interior of said cylindrical configuration defined by said screen means extending between said cylindrical plugs; and
    said screen means being positioned directly in the path of said fluid flowing from said inlet to said outlet, such that portions of said fluid pass through said screen means and through said beam of light while said gas bubbles contained within said portions of said fluid passing through said beam of light are separated from said fluid passing through said screen means and are prevented from entering said beam of light by flowing around the perimeter of said screen means without being removed from that portion of said fluid not passing through said beam of light.

2. The blood leak detector according to claim 1 wherein said screen means comprises a 70 micron stainless steel screen.

3. The blood leak detector according to claim 2 wherein said light beam generating means generates a green light beam, and wherein said light beam detecting means is responsive to green light.

4. The blood leak detector according to claim 1 wherein each of said cylindrical plugs further includes a filter mounted at the inner end thereof, and wherein said screen means further functions to cause fluid flow across the surfaces of said filters thereby tending to prevent the build-up of foreign materials on the surfaces of said filters.

5. The blood leak detector according to claim 4 wherein said cylindrical plugs and said screen means are positioned substantially above said bottom wall of said housing so as to permit accumulation of foreign materials in the bottom of said housing without interfering with the passage of light from said light beam generating means to said light beam detecting means.

6. The blood leak detector according to claim 1 wherein said light beam generating means comprises a light source and a green filter mounted in one of said plugs and wherein said light detecting means comprises a clear filter and a light sensitive device mounted in the other one of said plugs.

* * * * *